United States Patent [19]

Desai et al.

[11] 4,347,735
[45] Sep. 7, 1982

[54] PROCESS FOR MONITORING SOLVENT CONTENT OF GREEN CERAMIC SHEET, AND APPARATUS THEREFOR

[75] Inventors: Kamalesh S. Desai, Wappingers Falls; George E. Melvin, Poughkeepsie, both of N.Y.

[73] Assignee: International Business Machines Corporation, Armonk, N.Y.

[21] Appl. No.: 216,044

[22] Filed: Dec. 15, 1980

[51] Int. Cl.³ .................... G01N 3/20; G01N 33/38
[52] U.S. Cl. ............................. 73/73; 73/159; 73/849
[58] Field of Search ............... 73/73, 159, 849, 852, 73/854

[56] References Cited

U.S. PATENT DOCUMENTS

| | | |
|---|---|---|
| 1,903,716 | 4/1933 | Kalle . |
| 2,506,048 | 5/1950 | Akker ................................. 73/852 |
| 3,385,106 | 5/1968 | Fargo et al. |
| 3,677,076 | 7/1972 | Herzhoff et al. .................... 73/159 |
| 3,938,382 | 2/1976 | Takada et al. |

FOREIGN PATENT DOCUMENTS

| | | | |
|---|---|---|---|
| 190377 | 7/1964 | Sweden .................................. 73/73 |
| 280961 | 5/1971 | U.S.S.R. .............................. 73/849 |

*Primary Examiner*—Charles A. Ruehl
*Attorney, Agent, or Firm*—Wolmar J. Stoffel

[57] ABSTRACT

A process for monitoring solvent content in a ceramic green sheet wherein the green sheet is partially supported so that a portion of the sheet is free to sag under the influence of gravity, with or without any additional force to enhance or minimize the sag, measuring the rate of sag of the portion of the sheet free to sag, and comparing the rate of sag to a correlation standard of rate of sag versus solvent content of the green sheet under test to determine acceptability.

9 Claims, 2 Drawing Figures

PROCESS FOR MONITORING SOLVENT CONTENT OF GREEN CERAMIC SHEET, AND APPARATUS THEREFOR

DESCRIPTION

1. Technical Field

Our invention relates to multi-layer ceramic (MLC) technology, more particularly to process control and, in particular, to a technique for non-destructively monitoring solvent concentration in green ceramic sheet material, and apparatus for such monitoring.

In MLC technology, a plurality of punched and screened green ceramic sheets are laminated, and subsequently exposed to a sintering atmosphere where the binder and other organic components are burned off and the ceramic particles fused together. Unless the green sheets are properly dried before lamination, separation of the sheets may occur during the sintering operation which breaks the internal circuit continuity and renders the substrate useless. This invention will assist in checking and monitoring the solvent content in green ceramic sheets.

2. Background Art

Multi-layer ceramic technology is well known and is used to provide a substrate with an internal circuitry for joining a plurality of integrated circuit semiconductor devices in operative relation. The MLC substrate also has connection means, such as pins, for electrically joining the internal circuitry of the substrate to associated electrical elements. U.S. Pat. Nos. 3,726,002, 3,838,204, 3,999,004, and commonly-assigned application Ser. No. 053,477 describe and claim various techniques for producing MLC substrates, and also various MLC substrate features.

In this technology green sheets of ceramic, i.e. ceramic powder held together in sheet form by temporary organic binders are metallized with refractory metals, usually by screen printing. The metallized sheets are stacked, laminated, and fired to form a monolithic unit wth an internal circuit. This technology affords an opportunity to do three-dimensional wiring in what was formerly waste or inaccessible space in a ceramic substrate. As the semiconductor devices supported on the substrate become smaller and more complex, there is a corresponding need for providing a more dense, complex internal circuitry in the supporting MLC substrate. This in turn tightens up the processing requirements to assure continuity of the internal circuitry.

DISCLOSURE OF INVENTION

An object of the present invention is to provide a new technique for determining solvent concentration in a ceramic green sheet that is non-destructive of the green sheet.

Another object of this invention is to provide a simple, fast process for monitoring solvent in a ceramic green sheet and screened green sheet after drying that can be automated.

Yet another object of this invention is to provide a new apparatus for monitoring solvent content in a green ceramic sheet.

In accordance with the present invention of a process for monitoring solvent content in a ceramic green sheet, the green sheet is partially supported so that a portion of the sheet is free to sag under the influence of gravity, with or without any additional force to enhance or minimize the sag, measuring the rate of sag of the portion of the sheet free to sag, and comparing the rate of sag to a correlation standard of rate of sag versus solvent content of the green sheet under test to determine acceptability.

The apparatus of the invention for monitoring the solvent content of a green sheet has a means to support the green sheet so that a portion of the green sheet is free to sag, and a means to measure the rate of sag of the green sheet.

BRIEF DESCRIPTION OF DRAWINGS

The details of the invention will be described in connection with the accompanying drawing in which FIG. 1 discloses an apparatus embodiment for determining solvent content of a green sheet and also illustrates the process for monitoring.

BEST MODE FOR CARRYING OUT THE INVENTION

Figure 1:
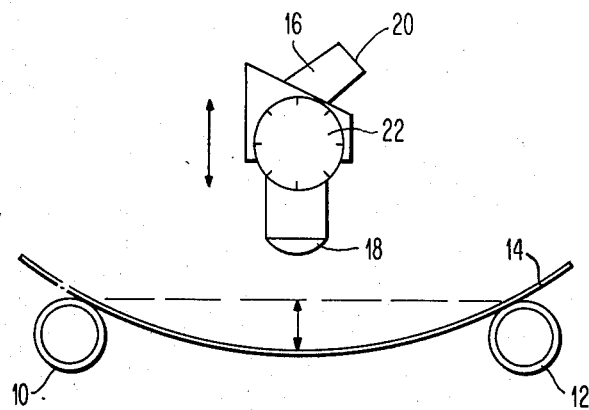

In MLC fabrication, green ceramic sheets are doctor bladed from a slurry containing particulate ceramic and glass material, an organic binder such as polyvinylbutyral, a solvent for the binder, and a plasticizer. Following the doctor blading operation the cast sheet, in the form of a continuous ribbon, is dried to remove most of the solvent. The resultant sheet is relatively pliable. The dried sheet is punched forming via holes, and a pattern screened on one or both surfaces, at the same time filling the via holes. Subsequently, the green sheets are assembled, pressed together, and the excess sheet trimmed away. The resultant green substrate is then sintered at a temperature in the range of 1250° to 1600° C. for a time sufficient to remove the binder, any remaining solvent, and plasticizer, and to fuse the glass and ceramic particles into a monolithic structure.

It has been observed that on occasion the green ceramic sheets have separated during the sintering operation. Studies have proven that the separation was at least in part caused by excess solvent in the sheet. The solvent content in the sheet results from either insufficient drying of the green sheet after doctor blading to remove the solvent originally in the slurry, or from solvent from the paste screened on the sheet after the via holes were punched. The latter solvent source is the most troublesome because the amount of conductive paste screened on each sheet and the associated solvent will vary with the nature of the sheet. For example, on ground plane and power plane sheets, a great deal of conductive paste is screened on the sheets. In contrast, with sheets that provide X and Y lines for signal lines, the amount of conductive paste is small. The same drying time may be adequate for one type of sheet, but not for the other. The paste solvent is difficult to remove during the drying operation because it has a low vapor pressure and interacts or diffuses into the green sheet.

In a manufacturing environment, it is difficult to make certain that every green ceramic sheet, where the sheets have differing drying requirements, has a solvent content sufficiently low to assure that separation of sheets will not occur before or during sintering. In addition to human error in sheet processing, other factors can occur to render the solvent concentration in sheets to unacceptably high levels. For example, drying conditions vary with weather, humidity, temperature, etc., and the drying apparatus can malfunction. The problem is a serious one because a single separation in a substrate will break conductive line continuity and make it worthless. Overdrying the green sheets must be avoided because too much drying will drive the plasticizer out of the ceramic green sheets which adversely affects handling and stability of the sheets.

It is therefore apparent that it is important to monitor the solvent content of green sheets to prevent delamination. In addition, large variations in solvent concentration adversely affect the dimensional stability and the handling control of the sheets. Dimensional stability becomes more critical as the size dimensions of the vias and conductive lines become smaller.

The conventional method for determining solvent concentration is by weighing which is time consuming, tedious, and destructive of the sheet being tested. The process consists of (1) weighing the punched sheet, (2) weighing the screened sheet, and (3) weighing the dried screen sheet. If the solvent concentration of the paste is known, the solvent remaining in the sheet after the drying can be calculated from the values of the three aforementioned weighing procedures. Since the weight of the sheet is large in comparison to the solvent removed, the process is not very exact. Further, weighing constraints usually require weighing only a portion of the sheet, making it destructive of the sheet. The process is thus not suited for routine monitoring of green sheet on a manufacturing line.

The monitoring process of the invention is based on the concept that the solvent in the screening conductive paste, and also the solvent in the original ceramic slurry, softens up the binder resin material and thereby allows more relative movement of the ceramic and glass particles in the sheets. This freer movement of solid particles was found to be directly related to the rate of sag of an unsupported portion of the sheet.

In carrying out the process, a consistent manner of supporting the sheet, allowing for a portion thereof to sag, must be decided upon. A preferred technique is to support the ceramic sheet on two spaced rods that are highly polished to reduce friction. This preferred structure is disclosed in FIGS. 1 and 2 of the drawings.

Referring now to FIG. 1, there is illustrated a preferred embodiment of an apparatus to detect the rate of sag of a green sheet. The apparatus consists of two spaced rods 10 and 12 having highly polished surfaces on which a green sheet 14 is deposited for testing. Directly above the green sheet 14 is positioned a microscope 16 with the objective lens 18 directed toward the sheet and eyepiece 20 positioned for viewing the sheet by the operator. A knob 22 provided with suitable graduations is also provided to indicate the location of the focal plane of the microscope. In operation, the ceramic green sheet 14 to be evaluated is placed on rods 10 and 12, the sheet allowed to sag for a pre-determined time and the microscope focused to determine the location of the mid-point of the sheet. The mid-point of the sheet is determined from the graduations on knob 22. The microscope knob 22 had previously been set so that the point of focus on the plane level with the top surfaces of rods 10 and 12 is zero. The change in the mid-point of the sheet can easily be determined by reading the figures from knob 22 which indicate the distance that the sheet sagged. The microscope can be conveniently set at zero by placing a rigid plate on bars 10 and 12 that has a central opening beneath the microscope. On the bottom side of the plate there is provided a second sheet of material having a surface that can be focussed on by the microscope. When the microscope is focussed on the opening, the knob is set to zero. By this manner, the distance that the green ceramic sheet sags can be determined. The rate of sag of the sheet 14 can be determined when the distance of sag is combined with the time the measurement is made after the sheet is deposited on the bars. The standard for comparison of the rate of sag of an unknown sheet is determined by placing a ceramic green sheet having a solvent concentration within the specification called for. The rate of sag of the standard is used for evaluating subsequent sheets in the apparatus of FIG. 1.

Figure 2:
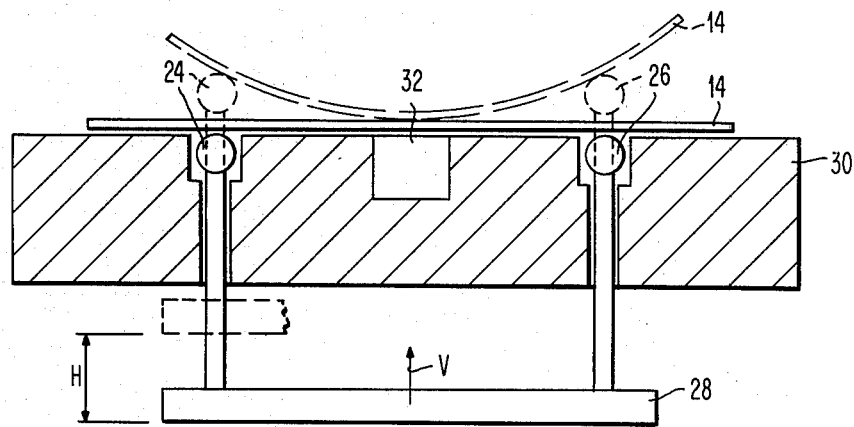
FIG. 2 depicts a second embodiment of the apparatus of the invention for monitoring solvents, which apparatus is adapted to be automated.

Referring now to FIG. 2 there is illustrated an embodiment of the apparatus of the invention that is adapted for automated monitoring. The platform 30 is preferably located in a line that conveys green sheet from the drying apparatus following the screening operation. The screened green sheet 14 is positioned over retracted spaced rods 24 and 26. The rods are then raised in unison by a suitable lift mechanism (not shown) acting on crossbar 28. The crossbar 28 is raised a distance H thereby lifting the sheet 14 as shown in dotted lines. After a pre-determined time interval, a suitable sensor 32 detects the location of the surface of the central portion of sheet 14. Sensor 32 can be any suitable device capable of determining the distance of the surface of the sheet from the top surface of the platform 30. Typically, the sensor can use sound waves reflected from the sheet to determine distance. Sensors of this type are well known and the structure per se does not constitute part of this invention.

In the practice of this invention the correlation between the rate of sag over a given time interval or, at a given instant, is determined for the specific green sheet that is considered having the proper solvent content. Preferably, a number of sheets with the proper solvent concentration are checked and the correlation determined by the average of the rate of sag data. Obviously, different correlations must be obtained when thickness of the sheet, different slurry compositions, and different slurry ingredients are involved. For example, a given solvent in a given concentration will have different effects on different resin binders. Also, differing amounts of plasticizers is different sets of green sheets will also affect the sag rate. A standard for the rate of sag must be obtained for the desired solvent concentration in each group of sheets where physical dimensions, concentration of ingredients vary.

The process of the invention is applicable to green ceramic sheets of any suitable thickness, preferably sheets with thicknesses in the range of 60 to 3 mils, more preferably from 15 to 6 mils. In the most preferred embodiment, the sheets will be supported on rods spaced a distance in the range of 2.0" to 6.0". However, other methods of supporting the sheet can be used in the practice of the invention.

The following example is presented to illustrate a preferred mode of practicing the invention and is not intended to unduly limit the scope of the claims of the invention.

EXAMPLE

Twenty green ceramic sheets were prepared from a slurry containing a mixture of $Al_2O_3$ and glass frit particles, a polyvinylbutyral resin, methyl alcohol and methyl isobutyl ketone solvents, and a plasticizer. The sheets, each 185 mm. sq. were dried and punched with via holes, and screened with a conductive paste which covered approximately 30% of the surface area.

The conductive paste was made up of 85% by weight molybdenum and molybdenum trioxide particles and 7.3% ink oil solvent. Ink oil is a product of American Mineral Spirits Company, sold uner the designation of AMSCO 10-550 ink oil. The total weight of the conductive paste on each sheet was approximately 2 grams. The total solvent, before drying, was 0.14 grams in the paste deposited on each sheet. The green ceramic sheets were separated into 5 groups of 4 sheets each and the groups dried in a batch drier at different time intervals at 75° C. in an air flow of 100 ft. per minute. The sheets after drying were placed on a pair of smooth rods spaced 4¾ inches apart and the rate of sag determined over an interval of 10 seconds, with the apparatus described and illustrated in FIG. 1. Immediately thereafter, a section of each sheet was cut away and the solvent concentration of the sheet determined by weighing techniques. Each of the section of sheets were weighed, the sheet dried for 60 minutes at 75° C. to drive out the remaining solvent, and the sheet weighed again. The solvent retained in the sheet at the time the sheet was tested was then determined by calculating the difference of the weights of the sheet before and after drying. The average of the Figs. of each of the four sheets was then calculated and the results recorded as follows:

| Group #1 | # of Sheets | Drying Time @ 75° C. | Sag Rate Over 10 Sec. Interval | Solvent Retained |
|---|---|---|---|---|
| 1 | 4 | 15 min. | .347 in. | .06 gr. |
| 2 | 4 | 30 min. | .248 in. | .032 gr. |
| 3 | 4 | 60 min. | .143 in. | .010 gr. |
| 4 | 4 | 90 min. | .111 in. | .005 gr. |
| 5 | 4 | 120 min. | .108 in. | .005 gr. |

A plot of solvent retained versus sag rate was made which can be used to determine the solvent concentration in the sheets tested where the sheets being monitored are the same type of sheets set forth in the example.

While the invention has been illustrated and described with reference to preferred embodiments thereof, it is to be understood that the invention is not limited to the precise construction herein disclosed and the right is reserved to all changes and modifications coming within the scope of the invention as defined in the appended claims.

We claim:

1. A process for determining the solvent content of a ceramic green sheet containing particulate ceramic material, an organic binder resin, and a solvent that interacts with the resin comprising,
    partially supporting a ceramic green sheet in a manner that a portion of the sheet is unsupported and free to sag,
    measuring the rate of sag of said portion of ceramic green sheet,
    comparing the rate of sag to a correlation of rate of sag versus solvent content for similar ceramic green sheets to determine solvent concentration.

2. The method of claim 1 wherein said ceramic green sheets have a screened-on pattern of conductive metal paste, which paste includes a solvent that interacts with said binder resin.

3. The method of claim 1 wherein said ceramic green sheet is supported on two spaced supports, with the spacing sufficient to permit sagging of the central portion of said ceramic green sheet.

4. The method of claim 3 wherein said spaced supports are rods with smooth polished surfaces.

5. The method of claim 1 wherein said unsupported ceramic green sheet sags under the sole influence of gravity.

6. An apparatus for determining the solvent content of a ceramic green sheet containing particulate ceramic material, an organic binder resin, and a solvent that interacts with the resin comprising,
    a means to support a ceramic green sheet in a manner that at least a portion of the sheet is free to sag under the influence of gravity,
    a means to determine the distance of sag of the unsupported portion of said ceramic green sheet over a timed interval and
    a correlation for the ceramic green sheet to be tested of rate of sag versus solvent content,
    the solvent content determined from a comparison of the measured distance of sag over a predetermined time interval to the rate of sag of said correlation.

7. The apparatus of claim 6 wherein said means to support a green sheet is comprised of two elongated spaced support elements have a smooth substantially frictionless surface.

8. The apparatus of claim 7 wherein said means to determine the distance of sag of the ceramic green sheet is a microscope provided with a means to indicate the plane of focus.

9. The apparatus of claim 6 which further includes a flat support, a means to extend and retract said elongated spaced support elements from positions above and below said flat surface.

* * * * *